United States Patent [19]

Diekmann

[11] Patent Number: 4,956,298
[45] Date of Patent: Sep. 11, 1990

[54] SEPARATION OR REACTION COLUMN UNIT

[76] Inventor: Stephan Diekmann, Wagenstieg 5, D-3400 Goettingen, Fed. Rep. of Germany

[21] Appl. No.: 296,737

[22] Filed: Jan. 13, 1989

[30] Foreign Application Priority Data

Jan. 13, 1988 [DE] Fed. Rep. of Germany ....... 8800301
Dec. 23, 1988 [DE] Fed. Rep. of Germany ....... 3843610

[51] Int. Cl.$^5$ ............................................. C12M 1/12
[52] U.S. Cl. ..................................... 430/311; 435/284;
435/296; 435/287; 427/102; 210/772
[58] Field of Search ............... 435/311, 284, 287, 296;
436/45, 174, 180; 206/546, 569, 229, 1.5, 505,
508; 215/DIG. 3, DIG. 8; 422/102, 9; 210/136,
772

[56] References Cited

U.S. PATENT DOCUMENTS

| | | | |
|---|---|---|---|
| 3,198,194 | 8/1965 | Wilburn | 215/DIG. 8 X |
| 3,239,089 | 3/1966 | Moylan | 215/DIG. 8 X |
| 3,410,444 | 11/1968 | Morane | 215/DIG. 8 X |
| 4,215,198 | 7/1980 | Gordon | 435/311 |
| 4,435,293 | 3/1984 | Graham, Jr. et al. | 210/772 |
| 4,436,631 | 3/1984 | Grahman, Jr. et al. | 210/772 |
| 4,464,254 | 8/1984 | Dojki et al. | 210/136 |
| 4,761,379 | 8/1988 | Williams et al. | 206/569 X |
| 4,775,629 | 10/1988 | Kuhl et al. | 435/311 X |
| 4,791,060 | 12/1988 | Chandler | 435/287 X |

Primary Examiner—Larry Jones
Attorney, Agent, or Firm—Foley & Lardner, Schwartz, Jeffery, Schwaab, Mack, Blumenthal & Evans

[57] ABSTRACT

A column unit is provided consisting of a centrifuging vessel and a receiving body with feed and discharge openings located at opposite ends. Desired column material is located within a middle portion of a hollow cylinder of the receiving body. A portion of the receiving body containing the discharge opening and the column material is received by the centrifuging vessel. The entire column unit is inserted into a conventional stand in a centrifuge. Accordingly, when sample material is introduced into the receiving body through the feed opening, it may flow without misdirection through the column material and discharge opening and into the centrifuge vessel.

25 Claims, 8 Drawing Sheets

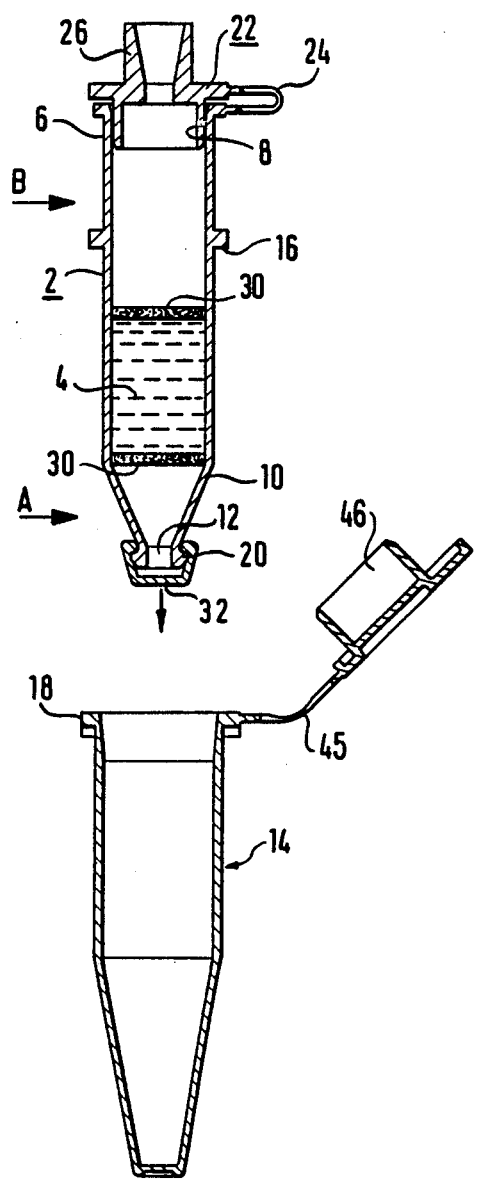
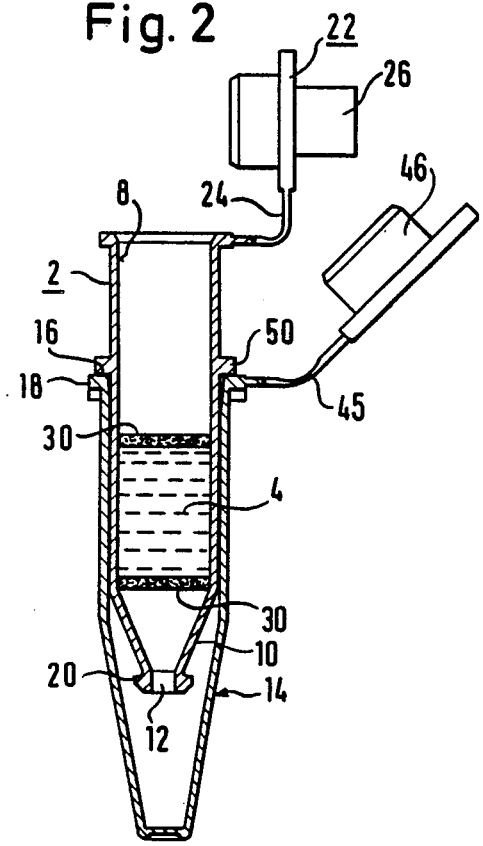
Fig. 1
Fig. 2

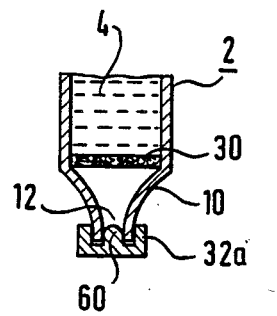
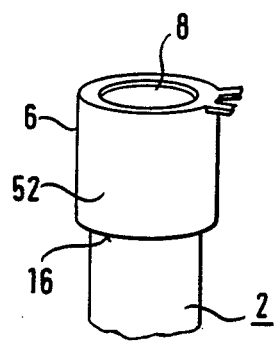
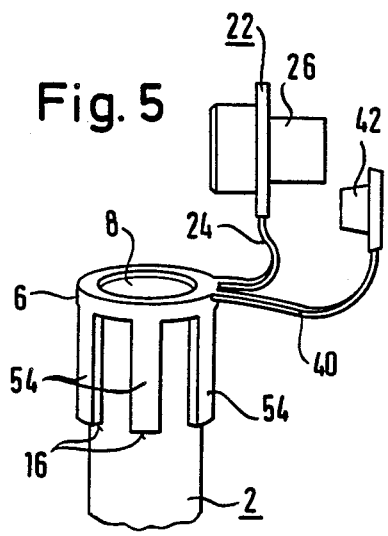

SEPARATION OR REACTION COLUMN UNIT

BACKGROUND OF THE INVENTION

The present invention relates to column unit for separating or reacting sample materials in a centrifuge.

In known separation or reaction column units, a receiving body is suspended by a holder over a centrifuging vessel for the sample material. The receiving body and the centrifuging vessel are not connected to each other. Accordingly, slipping of the receiving vessel may occur during elution, resulting in losses of the sample material from misdirected dripping of the eluate from the receiving body to the centrifuging vessel.

It is also known to perform various elutions in such separation or reaction column units. One such elution involves introducing a small volume of sample material with a comparatively large volume of elution buffer solution into the receiving vessel to rinse out the sample material from a column material. As a result of the release of sample material from the column material, the volume of the sample material is increased tenfold and usually has to be reduced for consequent reactions. Such a volume reduction is arduous, time-consuming and entails a loss of sample material.

SUMMARY OF THE INVENTION

Accordingly, it is an object of the present invention to provide a separation or reaction column unit for insertion in a centrifuge which does not require any special fastening.

Another object of the present invention is to prevent large increases in the volume of the sample material.

A further object of the present invention is to achieve separation efficiency and conversion which is comparable to currently known column units.

According to the present invention, the foregoing and additional objects are obtained by a column unit for insertion in a centrifuge to separate or react a sample material, comprising: a first vessel including a feed opening at a first end of the first vessel, a discharge opening at a second end of the first vessel, a hollow cylinder between the first and second ends and column material located within a middle portion of the hollow cylinder, wherein a sample material may flow through said feed opening, said column material, and said discharge opening; and a second vessel configured to fittingly receive a portion of the first vessel comprising the discharge opening and the middle portion of the hollow cylinder, wherein the sample material may flow through the discharge opening into the second vessel. The column unit may further comprise a projection located on the outer surface of the first vessel, the projection configured to contact an opening rim of the second vessel, wherein the second vessel has sufficient volume to receive the portion of the first vessel and the sample material which flows from the first vessel.

Other objects, features and advantages of the present invention will become apparent from the following detailed description. It should be understood, however, that the detailed description and specific examples, while indicating preferred embodiments of the present invention, are given by way of illustration only, since numerous changes and modifications will become apparent to those skilled in the art from this detailed description.

BRIEF DESCRIPTION OF THE DRAWINGS

FIG. 1 is a vertical section of an embodiment of the present invention showing a receiving body separate from a centrifuging vessel;

FIG. 2 is the vertical section of FIG. 1 showing a portion of the receiving body located within the centrifuging vessel;

FIG. 3 shows another embodiment of region A of FIG. 1;

FIG. 4 shows another embodiment of region B of FIG. 1;

FIG. 5 shows another embodiment of Region B of FIG. 1;

DETAILED DESCRIPTION OF THE PREFERRED EMBODIMENTS

Figure 6:
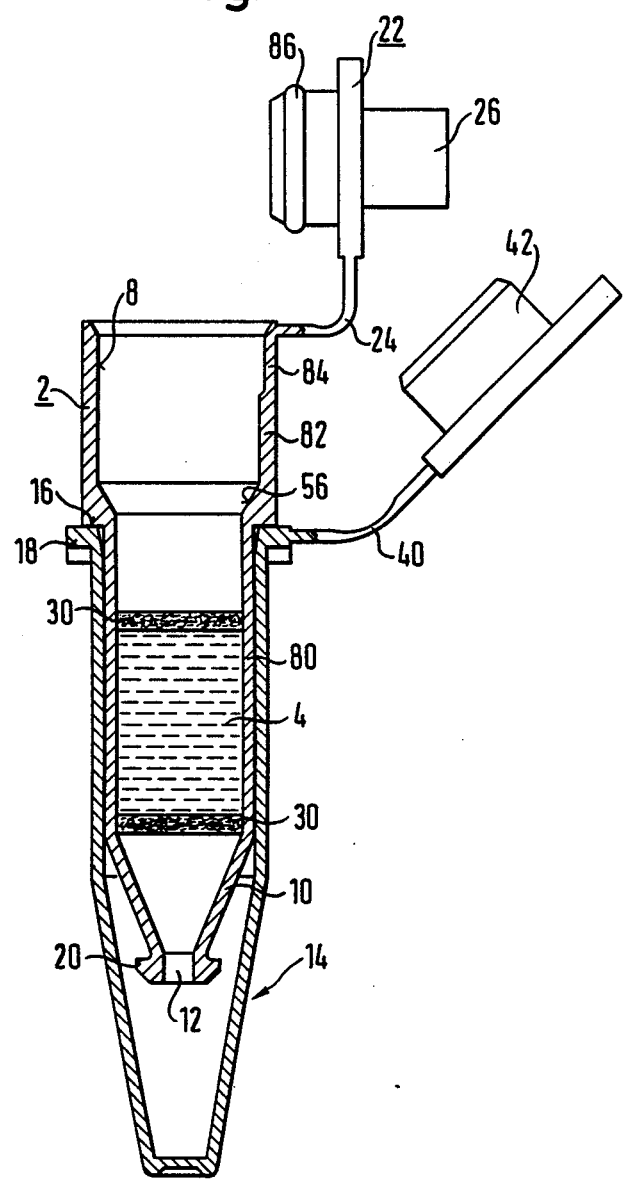
FIG. 6 shows another embodiment of the present invention.

According to the present invention, a column unit is provided consisting of a centrifuging vessel and a receiving body with feed and discharge openings located at opposite ends. Desired column material is located within a middle portion of a hollow cylinder of the receiving body. A portion of the receiving body containing the discharge opening and the column material is received by the centrifuging vessel. The entire column unit is inserted into a conventional stand in a centrifuge. Accordingly, when sample material is introduced into the receiving body through the feed opening, it may flow without misdirection through the column material and discharge opening and into the centrifuge vessel.

In the following description and accompanying drawings, like elements or features bear like reference numerals.

With reference to FIGS. 1 and 2, a column unit is seen to comprise a receiving body 2 and a centrifuging vessel 14. Centrifuging vessel 14 is sealed by a cap 46. Cap 46 is connected to the outer surface of centrifuging vessel 14 by flexible loop 45.

Receiving body 2 comprises a hollow cylinder which has column material 4 located within it. Receiving body 2 is bounded by an upper end 6 with a feed opening 8 for the introduction of sample material and by a lower end 10 with a discharge opening 12 for the exit of sample material after passage through column material 4. The column material 4 in the receiving body 2 lies between two fixed filters 30 which fill the entire diameter of the receiving body 2.

Column material 4 may be any material which causes a separation of the substances contained in the sample material, reacts with the sample material or catalyses the sample material. For example, column material 4 may be modified agarose, to which antibodies against a certain antigen contained in the sample material are coupled. During the flow of the sample material through the column material, these antigens are bonded to the antibodies and thereby held by the column material. The passed sample material is then free from these antigens. Another example of column material 4 is an enzyme such as RNase. If a sample solution containing RNA and DNA is introduced into receiving body 2, the RNA is broken down by the RNase while the DNA passes through the column material unchanged and can subsequently be isolated free from long RNA chains. Further examples of column materials which can be used are modified cellulose, hydroxyapatite and affinity adsorbents.

The separation or reaction column unit is in this case designed such that it fits as a unit into a conventional stand of a centrifuge. Before use, a liquid dead volume of the unit can be centrifuged out of the unit. The sample material is then introduced to receiving body 2 via feed opening 8, and (if appropriate, after a dwell time in the column material 4) centrifuged out of the column material 4 via discharge opening 12 and collected in the centrifuging vessel 14. Should it be necessary for improving the elution of the sample material, subsequent rinsing with a small volume of buffer solution can also be carried out.

A closure cap 32 for sealing discharge opening 12 can be fitted into the lower end 12 of the receiving body 2 and held in position by bead 20. At the upper end 6 of the receiving body 2, a removable feed opening cap 22 is fastened via a loop 24 on the receiving body 2. Cap 22 is provided with a conventional attachment 26 which allows a syringe to be attached to introduce sample material through feed opening 8. Attachment 26 may be connected to or integrally formed with cap 22. A cap 42 (FIG. 5) is provided to close the standard attachment 26. With reference to FIG. 5, cap 42 is fastened on the upper end 6 of the receiving body 2 by a flexible loop 40. These caps 22, 32, and 42 allow receiving body 2 to be sealed for storage.

As shown in FIG. 3, the lower end 10 of the receiving body 2 may have no circumferential bead 20. Rather, a closure cap 32a, with a protuberance 60 engaging the discharge opening 12, is provided for sealing discharge opening 12.

With reference to FIG. 2, receiving body 2 has a stop projection 16 which contacts an opening rim 18 of centrifuging vessel 14. Stop projection 16 may be formed by a thickening 52 of the upper end 6 of the receiving body 2, as shown in FIG. 4. Stop projection 16 may be longitudinal bars 54 on the upper part of the receiving body 2, as shown in FIG. 5. Stop projection 16 prevents receiving body 2 from being inserted too far into centrifuging vessel 14. After insertion of receiving body 2, centrifuging vessel 14 has sufficient volume to retain the sample material flowing from discharge opening 12 into vessel 14.

Stop projection 16 may be formed by a step-shaped widening 82 of the receiving body 2 in the direction of the feed opening 8, as shown in FIG. 6. The outside diameter of the receiving body 2 below the stop projection 16 in the region 80 is thus smaller than the outside diameter of the step-shaped widening 82. On the inside, the step-shaped widening 82 tapers towards the region 80 in the form of a cone 56. The wall thickness of the regions 80 and 82 are constant all around and are preferably the same as each other. In the region of the feed opening 8, the inside diameter may be lessened with reduction of the wall thickness at section 84 in order to receive an annular bead 86 on the feed opening cap 22.

Figure 7:
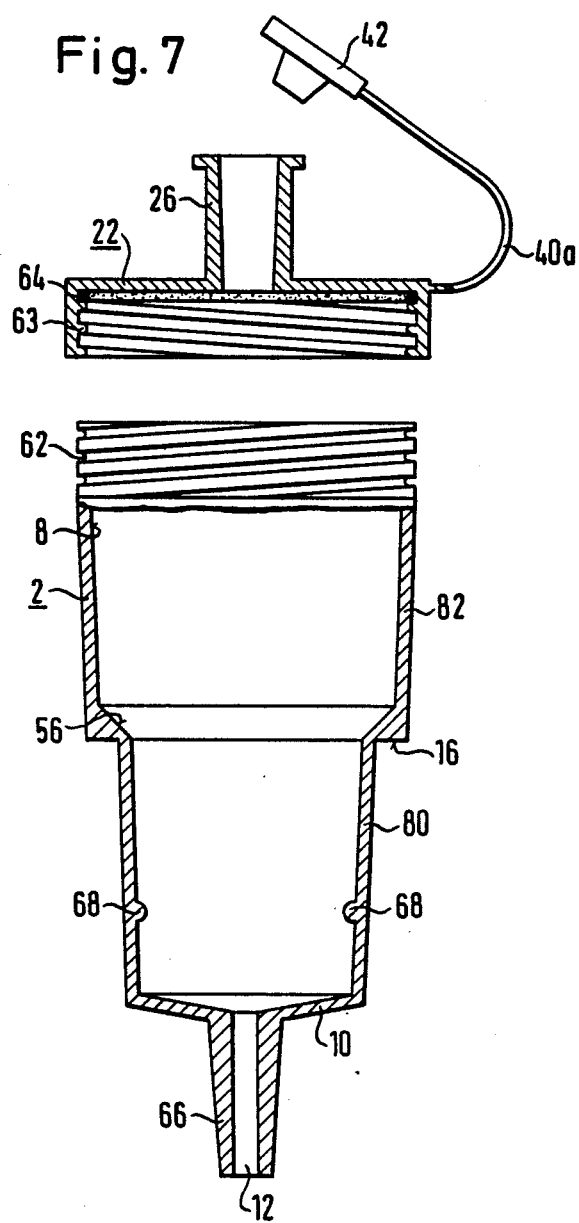
FIG. 7 shows another embodiment of the receiving body.

Feed opening cap 22 may be designed to be screwed onto the feed opening 8 of the receiving body 2, as seen in FIG. 7. For this purpose, the feed opening cover 22 has an internal thread 63, and the receiving body 2 is provided in the region of the feed opening 8 with a corresponding external thread 62. A sealing ring 64 is placed in the base of internal thread 63. Thus, cap 22 may easily be removed or secured to receiving body 2. Cap 42 can be fitted into the standard attachment 26 and joined to cap 22 by loop 40a.

In the lower region of the interior of receiving body 2, beads or lugs 68 are located for the fixing of mechanical blocks or filters 30 above and below column material 4.

These mechanical blocks 30 prevent column material from being displaced from receiving body 2 during centrifuging. Examples of mechanical blocks 30 include filters and glasswool. If no mechanical blocks 30 are provided, discharge opening 12 must have a diameter smaller than that of the particles of column material 4. Thus, it is preferable to use mechanical blocks or filters 30 so that column material 4 may have smaller particles if desired.

The lower end 10 of the receiving body 2 merges integrally with a standard syringe fitting 66.

Figure 8:
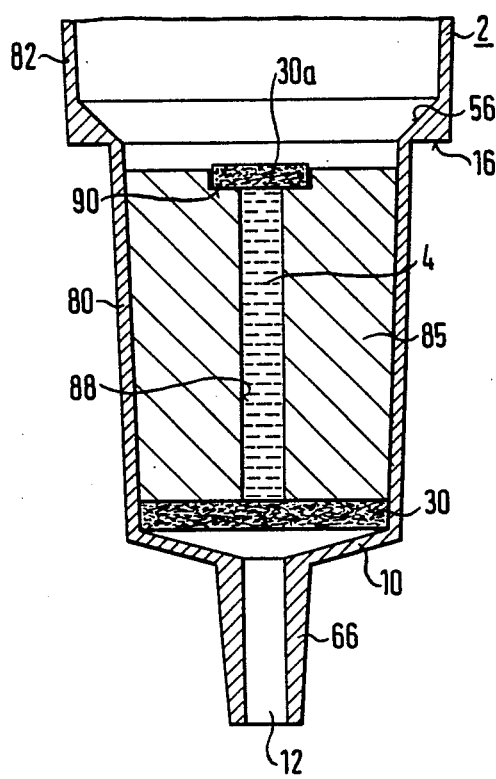
FIG. 8 shows an embodiment of the lower region of the receiving body.

With reference to FIG. 8, in the receiving body there is an insert body 85, provided with an axial channel 88 for receiving the column material 4 and bearing with a circumferential surface against the inside surface of the receiving body 2. This insert body 64 has the effect of constricting the flow cross-section of the sample material. Underneath the insert body 64 there is a mechanical block 30, e.g. a filter or glasswool, which extends over the entire inner cross-section of the receiving body 2. The upper end of the axial channel 88 is surrounded by a shoulder 90 in the insert body 85, which serves as support of a filter 30a of relatively small diameter.

Figure 9:
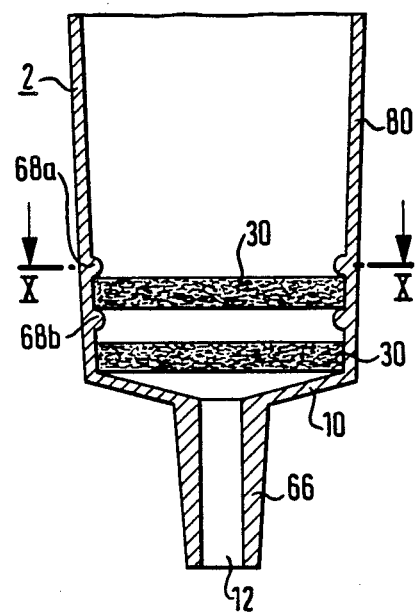
FIG. 9 shows another embodiment of the lower region of the receiving body.
Figure 10:
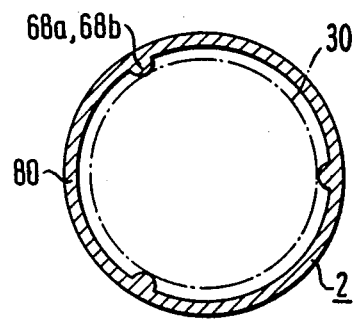
FIG. 10 shows a section along the line x—x of FIG. 9.

With reference to FIG. 9 and 10, in the lower region of the receiving body 2, interacting beads or lugs 68a and 68b are provided on the inside surface of the receiving body 2 for holding an upper filter 30.

Figure 11:
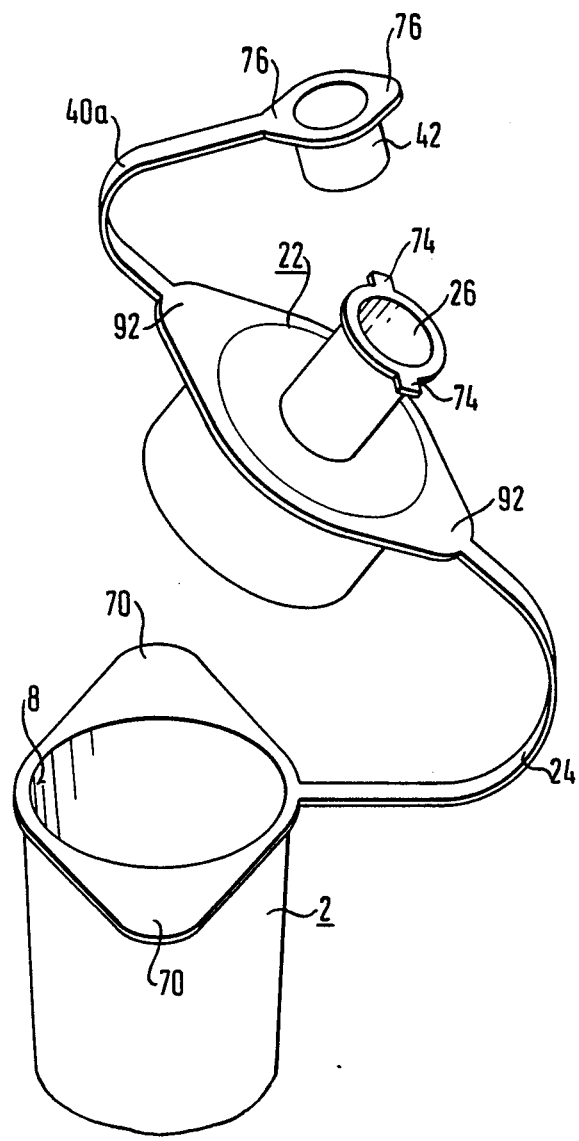
FIG. 11 shows the upper region of an embodiment of the receiving body.

With reference to FIG. 11, radially projecting gripping tabs 92 and 70, offset by 90°, for gripping with the hand are located, respectively, on the feed opening cover 22 and on the rim of the feed opening 8 of the receiving body 2. There are corresponding gripping tabs 76 on cap 42. The cap 42 is integrally joined to the feed opening cap 22 by a loop 40a.

Receiving body 2 may be configured to allow another receiving body 2 to be inserted, the discharge opening 12 of one receiving body 2 being placed inside the feed opening 8 of the other receiving body 12. Thus, efficient stacking of receiving bodies for storage or transportation is obtained.

With a concentric arrangement of the discharge opening in the lower end of the receiving body, occasionally small quantities of liquid remain in the receiving body above its lower end during centrifuging of the column unit. The elution effect is impaired as a result. During centrifuging, the column unit is turned such that the discharge opening lies for example 45° offset from the vertical, in any case such that no liquid remains in the receiving body during centrifuging.

Figure 12:
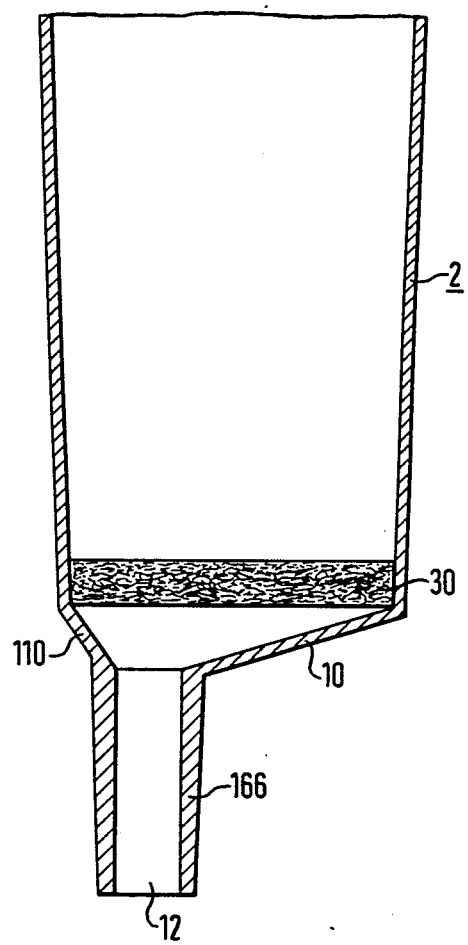
FIG. 12 shows another embodiment of the receiving body.

To prevent such impairment, lower end 10 of receiving body 2 is positioned to lead eccentrically to a standard syringe fitting 166, as shown in FIG. 12. This standard syringe fitting 166 is offset from the rim of the receiving body 2 near the region 110 of lower end 10 of the hollow-cylindrical receiving body 2.

The separation or reaction column unit according to the present invention thus makes possible a simple handling and effective elution of the sample material (in the separation method: firstly of the sample material not retained by the column material, then also of the retained sample material) with an extremely low increase in the sample volume.

What is claimed is:

1. A column unit for insertion in a centrifuge to separate or react a sample material, comprising:
   a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening;
   a second vessel configured to fittingly receiving a portion of said first vessel comprising said discharge opening and said middle portion of said hollow cylinder, wherein the sample material may flow through said discharge opening into said second vessel;
   a feed cap which seals said feed opening of said first vessel; and
   a means for attaching a syringe to said feed cap.

2. The column unit according to claim 1, further comprising a projection located on the outer surface of said first vessel, said projection configured to contact an opening rim of said second vessel, wherein said second vessel has sufficient volume to receive said portion of said first vessel and the sample material which flows from said first vessel.

3. The column unit according to claim 2, wherein said projection comprises a first bead located about the circumference on the outer surface of said first vessel.

4. The column unit according to claim 2, wherein said projection comprises a portion of the outer wall of said first vessel near said first end of said first vessel.

5. The column unit according to claim 2, wherein said projection comprises a portion of said hollow cylinder near said first end, said portion having an inner circumference greater than the inner circumference of said opening rim of said second vessel.

6. The column unit according to claim 1 further comprising a discharge cap which seals said discharge opening of said first vessel.

7. The column unit according to claim 6, wherein said cap fits about the outer circumference of said discharge opening, said cap having a protuberance which fits into said discharge opening of said first vessel.

8. The column unit according to claim 1, wherein said feed cap fits into said feed opening of said first vessel, said feed covering being connected to the outer wall of said first vessel near said feed opening via a feed cap flexible member.

9. The column unit according to claim 1, wherein said cap has an annular bead which fits into said feed opening.

10. The column unit according to claim 9, wherein the inner circumference of a portion of said first vessel near said feed opening is greater than the inner circumference of the remaining portion of said first vessel, whereby said annular bead contacts said inner circumference of said portion of said first vessel near said feed opening.

11. The column unit according to claim 1, wherein said feed cap is threaded and said feed opening is like threaded so as to engage said threaded feed cap.

12. The column unit according to claim 1, further comprising a first pair of tabs located at opposite locations on the rim of said feed opening of said first vessel and a second pair of tabs located on said feed cap each tab of said second pair being located at a right angle to each tab of said first pair.

13. The column unit according to claim 1, wherein said means for attaching is integrally joined to said feed cap.

14. The column unit according to claim 1, further comprising a removable cap for said means for attachment, said removable cap being connected to the outer wall of said first vessel near said feed opening via a first vessel flexible member.

15. The column unit according to claim 1, further comprising a removable cap for said means for attachment, said cap being connected to said feed cap via a cap flexible member.

16. The column unit according to claim 1, further comprising a removable cap for said means for attaching, said cap comprising radially projecting tabs.

17. The column unit according to claim 1, further comprising a multiplicity of first vessels, said feed opening of each of said first vessels being configured to receive said discharge opening of each of said first vessels.

18. A column unit for insertion in a centrifuge to separate or react a sample material, comprising:
   a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening;
   a second vessel configured to fittingly receiving a portion of said first vessel comprising said discharge opening and said middle portion of said hollow cylinder, wherein the sample material may flow through said discharge opening into said second vessel; and
   a projection located on the outer surface of said first vessel, said projection configured to contact an opening rim of said second vessel, wherein said second vessel has sufficient volume to receive said portion of said first vessel and the sample material which flows from said first vessel, wherein said projection comprises bars which extend longitudinally along said outer surface of said first vessel near said first end.

19. A column for insertion in a centrifuge to separate or react a sample material, comprising:
   a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening;
   a second vessel configured to fittingly receiving a portion of said first vessel comprising said discharge opening and said middle portion of said hollow cylinder, wherein the sample material may flow through said discharge opening into said second vessel;

a discharge cap which seals said discharge opening of said first vessel; and a bead located about the outer circumference of said discharge opening, whereby said cap fits about said bead and seals said discharge opening of said first vessel.

20. A column unit for insertion in a centrifuge to separate or react a sample material, comprising:

a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening;

a second vessel configured to fittingly receiving a portion of said first vessel comprising said discharge opening and said middle portion of said hollow cylinder, wherein the sample material may flow through said discharge opening into said second vessel; and wherein said column material located within said middle portion of said first vessel is located between two filters, said filters being fixed to the inner walls of said first vessel.

21. The column unit according to claim 20, further comprising a filter located at each end of said axial channel of said insert body, said filters being supported by supporting elements located at each open end of said axial channel.

22. A column unit for insertion in a centrifuge to separate or react a sample material, comprising:

a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening;

a second vessel configured to fittingly receiving a portion of said first vessel comprising said discharge opening and said middle portion of said hollow cylinder, wherein the sample material may flow through said discharge opening into said second vessel; and an insert body located within said middle portion of said hollow cylinder of said first vessel, said insert body having an axial channel having two open ends for containment of said column material, said insert body having an outer circumference which abuts the inner circumference of said middle portion.

23. A column unit for insertion in a centrifuge to separate or react a sample material, comprising:

a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening; and a second vessel configured to fittingly receiving a portion of said first vessel comprising said discharge opening and said middle portion of said hollow cylinder, wherein the sample material may flow through said discharge opening into said second vessel;

wherein said discharge opening of said first vessel has an inner circumference which is less than the inner circumference of said second end of said first vessel, said discharge opening configured to attach a syringe.

24. A column unit for insertion in a centrifuge to separate or react a sample material, comprising:

a first vessel including a feed opening at a first end of said first vessel, a discharge opening at a second end of said first vessel, a hollow cylinder between said first and second ends and column material located within a middle portion of said hollow cylinder, wherein a sample material may flow through said feed opening, said column material, and said discharge opening; and a second vessel configured to fittingly receiving a portion of said first vessel comprising said discharge opening and said middle portion of said hollow cylinder, wherein the sample material may flow through said discharge opening into said second vessel;

wherein said discharge opening of said first vessel and said second end of said first vessel are eccentric.

25. The column unit according to claim 24, further comprising a means for attaching a syringe, said means for attaching extending from said discharge opening of said first vessel.

* * * * *